United States Patent

Berrer

[11] 4,007,032
[45] Feb. 8, 1977

[54] HERBICIDALLY ACTIVE TRIAZIN-DERIVATIVES

[75] Inventor: Dagmar Berrer, Riehen, Switzerland

[73] Assignee: Ciba-Geigy Corporation, Ardsley, N.Y.

[22] Filed: July 21, 1975

[21] Appl. No.: 597,608

[30] Foreign Application Priority Data

July 25, 1974 Switzerland .................. 10268/74

[52] U.S. Cl. .................. 71/93; 260/249.6; 260/249.8
[51] Int. Cl.² .................. A01N 9/22; C07D 251/52; C07D 251/66
[58] Field of Search .................. 260/249.6, 249.8; 71/93

[56] References Cited

UNITED STATES PATENTS 3,873,544  3/1975  Kuehne et al. .................. 260/249.6

FOREIGN PATENTS OR APPLICATIONS 955,511  4/1964  United Kingdom

*Primary Examiner*—John M. Ford
*Attorney, Agent, or Firm*—Harry Falber

[57] ABSTRACT

This invention discloses new triazine derivatives, to herbicidal compositions containing them and to a method for selectively controlling weeds in cultivated crops with them.

The triazine derivatives correspond to the formula I

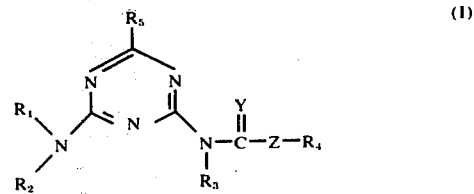

wherein
$R_1$ represents hydrogen, $C_1$–$C_6$-alkyl, $C_3$–$C_6$-cycloalkyl, $C_4$–$C_7$-cycloalkylalkyl, $C_2$–$C_6$-alkoxyalkyl, $C_2$–$C_6$-cyanoalkyl, $C_3$–$C_4$-alkenyl or $C_3$–$C_4$-alkynyl,
$R_2$ represents hydrogen or $C_1$–$C_6$-alkyl,
$R_3$ represents hydrogen or $C_1$–$C_6$-alkyl,
$R_4$ represents $C_1$–$C_6$-alkyl, $C_3$–$C_6$-cycloalkyl, $C_2$–$C_6$-alkoxyalkyl, $C_2$–$C_6$-cyanoalkyl or $C_1$–$C_6$-halogenoalkyl,
$R_5$ represents methoxy, ethoxy, methylthio, ethylthio or azido ($N_3$), and
Y and Z each independently represent sulphur or oxygen.

9 Claims, No Drawings

HERBICIDALLY ACTIVE TRIAZIN-DERIVATIVES

The present invention relates to new triazine derivatives, to processes for producing them, as well as to compositions and to processes for the selective control of weeds in useful crops and for the control of pests.

The triazine derivatives correspond to the formula I

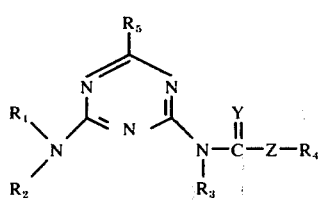

wherein
R₁ represents hydrogen, $C_1$–$C_6$-alkyl, $C_3$–$C_6$-cycloalkyl, $C_4$–$C_7$-cycloalkylalkyl, $C_2$–$C_6$-alkoxyalkyl, $C_2$–$C_6$-cyanoalkyl, $C_3$–$C_4$-alkenyl or $C_3$–$C_4$-alkynyl,
R₂ represents hydrogen or $C_1$–$C_6$-alkyl,
R₃ represents hydrogen or $C_1$–$C_6$-alkyl,
R₄ represents $C_1$–$C_6$-alkyl, $C_3$–$C_6$-cycloalkyl, $C_2$–$C_6$-alkoxyalkyl, $C_2$–$C_6$-cyanoalkyl or $C_1$–$C_6$-halogenoalkyl,
R₅ represents methoxy, ethoxy, methylthio, ethylthio or azido (N₃), and
Y and Z each independently represent sulphur or oxygen.

The triazine derivatives of the formula I are new. Similar compounds in which R₅ represents chlorine, methyl or a chlorinated methyl are described in the Swiss Pat. Specification No. 433,860, which corresponds to the British Pat. Specification No. 955,511 or to the French Pat. Specification No. 1,322,484.

In the definitions of the formula I, there are meant by alkyl or as alkyl moiety of a cycloalkylalkyl, alkoxyalkyl, cyanoalkyl or halogenoalkyl group, depending on the number of the given carbon atoms, e.g., the following groups: methyl, ethyl, propyl, butyl, pentyl or hexyl, as well as isomers thereof, such as iso-propyl, iso-, sec.- or tert.-butyl, 1-methylbutyl, 1,2-dimethylpropyl, etc..

To be mentioned as alkoxy moiety of an alkoxyalkyl group are, e.g., methoxy, ethoxy, propoxy or butoxy, as well as their isomers such as iso-propoxy and iso-, sec- or tert.butoxy.

By $C_3$–$C_4$-alkenyl are meant, e.g., the following groups: allyl, butenyl, methallyl or prop-1-enyl, as well as isomers thereof such as iso-propenyl or 2-methyl-prop-1-enyl.

$C_3$–$C_4$-Alkynyl denotes, e.g., the following groups: propargyl or butin-1-yl-3.

As cycloalkyl or as cycloalkyl moiety of a cycloalkylalkyl group there may be mentioned, e.g., the following groups: cyclopropyl, cyclobutyl, cyclopentyl or cyclohexyl. The term halogen signifies fluorine, chlorine, bromine or iodine. In the case of the halogenoalkyl groups, mention is made, e.g., of the trifluoromethyl, difluorochloromethyl and trichloroethyl groups.

An interesting group of compounds of the formula I comprises those wherein R₅ denotes methylthio. Of interest are likewise compounds of the formula I wherein R₅ represents methoxy or azido. A further important group of compounds of the formula I consists of those wherein R₁ represents $C_1$–$C_4$-alkyl, R₂ and R₃ represent hydrogen, R₄ represents $C_1$–$C_4$-alkyl, R₅ represents methylthio and Y and Z represent oxygen.

An individual compound particularly interesting as a selective herbicide is 2-t-butylamino-4-methylthio-6-methoxycarbonylamino-s-triazine of the formula

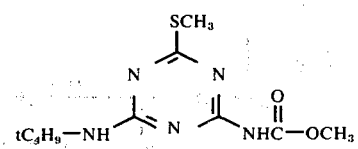

Likewise of interest are, e.g.:
2-ethyl-4-methylthio-6-methoxycarbonylamino-s-triazine, 2-i-propyl-4-methylthio-6-methoxycarbonylamino-s-triazine and 2-i-propyl-4-methoxy-6-methoxycarbonylamino-s-triazine.

The compounds of the formula I can be produced by methods known per se from cyanuric chloride by replacing the three chlorine atoms present, successively and in any desired sequence, by the groups

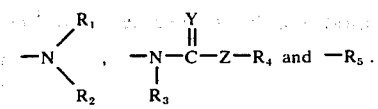

Thus, for the purpose of, e.g., introducing the substituent R₅, a compound of the formula II

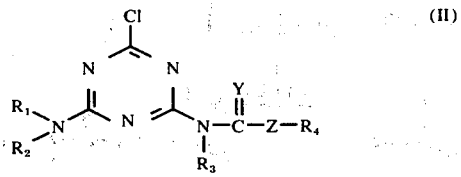

is reacted, in the presence of a base, with methyl mercaptan or ethyl mercaptan, with an alkali metal azide or with an alkali methylate or alkali ethylate.

Such reactions are performed at a temperature of 0°–80° C, preferably between 20° and 60° C, at normal pressure.

The reactions can be performed in the presence or absence of preferably anhydrous solvents or diluents inert to the reactants. Suitable such solvents or diluents are, for example, the following: aliphatic or aromatic hydrocarbons such as benzene, toluene, xylenes, petroleum ether; halogenated hydrocarbons such as chlorobenzene, methylene chloride, ethylene chloride or chloroform; ethers and ethereal compounds such as dialkyl ether, dioxane, tetrahydrofuran, ketones such as acetone, methyl ethyl ketone, nitriles such as acetonitrile; N,N-dialkylated amides such as dimethylformamide, dimethylsulphoxide, and mixtures of such solvents with each other.

The reactions are performed preferably in the presence of a base. There can be mentioned as such, in particular, nitrogen bases such as pyridine and tertiary amines, especially trimethylamine.

One of the methods for the introduction of the group

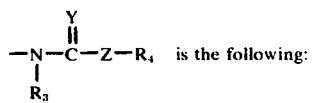 is the following:

Method I ( 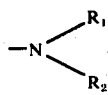 represents the s-triazine ring with the corresponding valence )

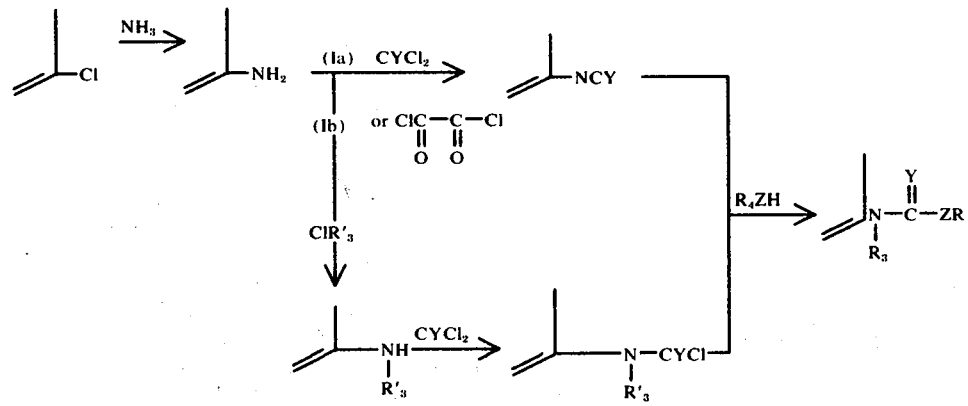

Other methods can be represented as follows:

Method II

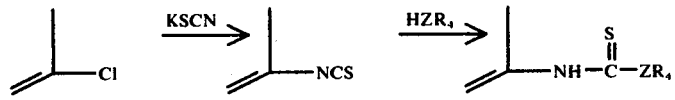

Method III

Method IV

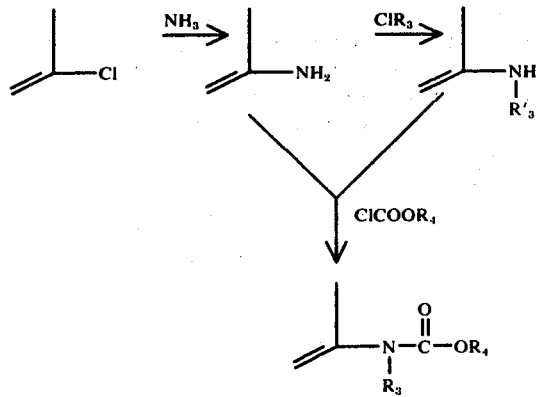

The group $$-N\begin{matrix}R_1\\R_2\end{matrix}$$

can be introduced, e.g., by the use of corresponding amines, or by other known methods. Where not otherwise stated, the symbols $R_1$, $R_2$, $R_3$, $R_4$, $R_5$, Y and Z have the meanings given under formula I. The symbol $R_3'$ stands for $C_1$–$C_6$-alkyl.

The compounds of the formula I can be used for the control of various plant and animal pests.

A number of the compounds of the formula I can be employed as insecticides and acaricides, which combat, in particular, larvae and nymphs.

Some of these compounds are effective in controlling phytopathogenic fungi.

Some of the active substances embraced by the formula I are suitable also as plant regulators, i.e. for influencing the development of the plant in the various stages of germination, blossom formation, fruit setting, growth inhibition, etc., as well as for the regulation of ripening, for fruit abscission, defoliation, desiccation and formation of plant components. There are thus observed, for example, growth inhibition in the case of grasses and desiccation in the case of cotton and potatoes.

The triazinyl derivatives of the formula I according to the invention possess however, in particular, herbicidal properties, and are especially suitable for the control of gramineous and broad-leaved weeds in various cultivated crops. Applied in higher concentrations, the new compounds act as total herbicides, in lower concentration, however, as selective herbicides. Weeds that are difficult to control and deep-rooted annual and perennial weeds are successfully checked in growth or destroyed by the active substances of the formula I. The new active substances can be applied, with equally good success, either before germination (pre-emergence) or after germination (postemergence). Thus, field weeds, such as millet varieties (Panicum sp.), wild oat (Avena fatua), mustard varieties (Sinapis sp.), goosefoot varieties (Chenopodiaceae), slender foxtail varieties, e.g. Amaranthus sp., grasses, e.g. Lolium sp., compositae, e.g. Taraxacum sp., and wild chamomile varieties (Matricaria sp.), can be destroyed or hindered in growth without damage being caused to useful plants, such as cereals, maize, cotton, sorghum, soya beans, etc.. The amounts applied vary and are dependent on the time of application: they are between 0.1 and 10 kg of active substance per hectare — with application before germination (pre-emergence) of the plants up to 4 kg of active substance per hectare, and after germination (postemergence) of the plants 1 to 5 kg of active substance per hectare. For the total destruction of the entire crop of weeds, for example on adjacent fallow land, it is necessary to apply more than 10 kg of active substance per hectare.

The compounds of formula I can be used on their own or together with suitable carriers and/or additives. Suitable carriers and additives may be solid or liquid, and they correspond to the substances common in formulation practice, such as natural and regenerated mineral substances, solvents, dispersing agents, wetting agents, adhesives, thickeners, binders and/or fertilisers.

The compositions according to the invention are produced in a manner known per se by the intimate mixing and/or grinding of active substances of the general formula I with suitable carriers, optionally with the addition of dispersing agents or solvents that are inert to the active substances. The active substances can be obtained and used in the following forms:
solid preparations:
  dusts, scattering agents, granulates, coated granulates, impregnated granulates and homogeneous granulates;
water-dispersible active-substance concentrates:
  wettable powders, pastes or emulsions;
liquid preparations:
  solutions.

Other biocidal active substances or compositions can be mixed with the described compositions of the invention. Thus, for the broadening of their sphere of action, the new compositions may contain, in addition to the stated compounds of the general formula I, for example insecticides, fungicides, bactericides, fungistatics, bacteriostatics or nematocides. The compositions of the invention can moreover contain fertilisers, trace elements, etc..

Preparations of the new active substances of the general formula I are described in the following. Parts denote parts by weight.

Dusts:
The following substances are used to produce (a) a 5% dust, and (b) a 2% dust:
  a. 5 parts of active substance,
     95 parts of talcum;
  b. 2 parts of active substance,
     1 part of highly dispersed silicic acid,
     97 parts of talcum.

The active substances are mixed and ground with the carriers.

Granulate:
The following substances are used to produce a 5% granulate:
  5 parts of active substance,
  0.25 parts of epichlorohydrin,
  0.25 part of cetyl polyglycol ether,
  3.50 parts of polyethylene glycol,
  91 parts of kaolin (particle size 0.3 - 0.8 mm).

The active substance is mixed with epichlorohydrin and dissolved with 6 parts of acetone; the polyethlene glycol and cetyl polyglycol ether are then added. The solution thus obtained is sprayed onto kaolin, and the acetone is subsequently evaporated off.

Wettable powder:
The following constituents are used to prepare (a) a 40%, (b) and (c) a 25%, and (d) a 10% wettable powder:
  a. 40 parts of active substance,
     5 parts of sodium lignin sulphonate,
     1 part of sodium dibutyl-naphthalene sulphonate,
     54 parts of silicic acid;
  b. 25 parts of active substance No. 1,
     4.5 parts of calcium lignin sulphonate,
     1.9 parts of Champagne chalk/hydroxyethyl cellulose mixture (1:1),
     1.5 parts of sodium dibutyl naphthalene sulphonate,
     19.5 parts of silicic acid,
     19.5 parts of Champagne chalk,
     28.1 parts of kaolin;
  c. 25 parts of active substance No. 1,
     2.5 parts of isooctylphenoxy-polyoxyethylene-ethanol,
     1.7 parts of Champagne chalk/hydroxyethyl cellulose mixture (1:1),
     8.3 parts of sodium aluminium silicate,
     16.5 parts of kieselguhr,
     46 parts of kaolin;
  d. 10 parts of active substance,
     3 parts of a mixture of the sodium salts of saturated fatty alcohol sulphates,
     5 parts of naphthalenesulphonic acid/formaldehyde condensate,
     82 parts of kaolin.

The active substances are intimately mixed in suitable mixers with the additives; the mixture is then ground in the appropriate mills and rollers. Wettable powders are obtained which can be diluted with water to give suspensions of any desired concentration. Such diluted active-substance suspensions can be used, for example, for the control of Avena fatua in useful crops.

EMULSIFIABLE CONCENTRATE

The following substances are used to produce a 25% emulsifiable concentrate:
25 parts of active substance,
2.5 parts of epoxidised vegetable oil,
10 parts of alkylarylsulphonate/fatty alcohol polyglycol ether mixture,
5 parts of dimethylformamide,
57.5 parts of xylene.

It is possible to prepare from such concentrates, by dilution with water, emulsions of any desired concentration.

The invention is further illustrated by the following Examples without its scope being limited by them. The temperature values are given in degrees Centigrade.

EXAMPLE 1

Production of 2-t-butylamino-4-methylthio-6-methoxycarbonylamino-s-triazine of the formula

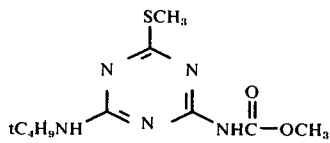

(Compound No. 1)

485 g (1.68 moles) of 2-t-butylamino-4-chloro-6-methoxycarbonylamino-s-triazine is placed into 400 ml of absolute acetone, and at 20°–25° there is then added dropwise 99 g (1.68 mole) of 100% trimethylamine in 500 ml for absolute acetone. The reaction mixture is stirred for 45 minutes, and there is subsequently added dropwise at 20° – 25° 80.6 g (1.65 moles) of methylmercaptan dissolved in 400 ml of absolute acetone. After a further 2 hours' stirring, about 50% of the acetone is distilled off in vacuo and the residue is poured into 2½ litres of water. The precipitated product (Compound No. 1) is filtered off, washed with water, dried, and recrystallised from heptane; m.p. 128°–130°.

EXAMPLE 2

Production of 2-ethylamino-4-ethoxycarbonylamino-6-azido-s-triazine of the formula

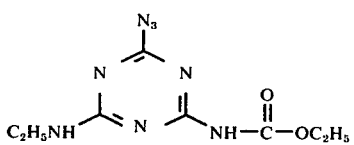

(Compound No. 2).

43.3 g (0.177 mole) of 2-ethylamino-4-ethoxycarbonylamino-6-chloro-s-triazine is placed into 200 ml of absolute acetone; there are then added dropwise at 20° – 25° 10.6 g (0.177 mole) of 100% trimethylamine dissolved in 30 ml of absolute acetone, and immediately afterwards a solution of 11.5 g (0.177 mole) of Na N$_3$ in 50 ml of water. The resulting suspension of the Compound No. 2 is poured into 1 litre of water; the product is filtered off, washed with water, dried, and recrystallised from acetonitrile; m.p. 131° – 133°.

The following compounds are produced in an analogous manner or by one of the processes described herein.

| Compound No. | R$_1$ | R$_2$ | R$_3$ | R$_4$ | R$_5$ | Y | Z | Physical data |
|---|---|---|---|---|---|---|---|---|
| 3 | C$_2$H$_5$ | H | H | CH$_3$ | SCH$_3$ | O | O | m.p. 119–121° |
| 4 | C$_2$H$_5$ | H | H | C$_2$H$_5$ | SCH$_3$ | O | O | m.p. 88–91° |
| 5 | CH$_3$ | H | H | CH$_3$ | SCH$_3$ | O | O | m.p. 168–170° |
| 6 | C$_2$H$_5$ | H | H | iC$_3$H$_7$ | SCH$_3$ | O | O | m.p. 98–100° |
| 7 | iC$_3$H$_7$ | H | H | CH$_3$ | SCH$_3$ | O | O | m.p. 116–117° |
| 8 | iC$_3$H$_7$ | H | H | iC$_3$H$_7$ | SCH$_3$ | O | O | m.p. 112–114° |
| 9 | C$_2$H$_5$ | H | H | CH$_3$OCH$_2$CH$_2$ | SCH$_3$ | O | O | m.p. 85–86° |
| 10 | iC$_3$H$_7$ | H | H | CH$_3$OCH$_2$CH$_2$ | SCH$_3$ | O | O | m.p. 90–91° |
| 11 | iC$_3$H$_7$ | H | H | —C(CH$_3$)(CH$_3$)—CN | SCH$_3$ | O | O | m.p. 114–116° |
| 12 | iC$_3$H$_7$ | H | H | CH$_2$CCl$_3$ | SCH$_3$ | O | O | m.p. 121–124° |
| 13 | sC$_4$H$_9$ | H | H | CH$_3$ | SCH$_3$ | O | O | m.p. 70–71° |
| 14 | —C(CH$_3$)(CH$_3$)—CN | H | H | CH$_3$ | SCH$_3$ | O | O |  |
| 15 | cyclopropyl | H | H | CH$_3$ | SCH$_3$ | O | O | m.p. 144–146° |
| 16 | C$_2$H$_5$ | H | H | cyclopropyl | SCH$_3$ | O | O |  |
| 17 | C$_2$H$_5$ | H | H | tC$_4$H$_9$ | SCH$_3$ | O | O |  |
| 18 | C$_2$H$_5$ | C$_2$H$_5$ | H | CH$_3$ | SCH$_3$ | O | O |  |
| 19 | CH$_3$—CH(CH$_3$)—CH(CH$_3$) | H | H | CH$_3$ | SCH$_3$ | O | O |  |
| 20 | C$_6$H$_{11}$—CH$_2$— | H | H | CH$_3$ | SCH$_3$ | O | O |  |
| 21 | CH$_2$—CH=CH$_2$ | H | H | CH$_3$ | SCH$_3$ | O | O |  |
| 22 | CH$_2$—C≡CH | H | H | CH$_3$ | SCH$_3$ | O | O |  |
| 23 | H | H | H | CH$_3$ | SCH$_3$ | O | O |  |
| 24 | tC$_4$H$_9$ | H | H | CH$_3$ | SC$_2$H$_5$ | O | O |  |
| 25 | C$_2$H$_5$ | H | H | C$_2$H$_5$ | SCH$_3$ | O | S | m.p. 171–173° |
| 26 | CH$_3$ | H | H | C$_2$H$_5$ | SCH$_3$ | O | S | m.p. 174° |
| 27 | CH$_3$ | H | H | CH$_3$ | SCH$_3$ | O | S | m.p. 190° (decomp.) |
| 28 | tC$_4$H$_9$ | H | H | CH$_3$ | SCH$_3$ | O | S | m.p. 192–193° |

-continued

| Compound No. | R₁ | R₂ | R₃ | R₄ | R₅ | Y | Z | Physical data |
|---|---|---|---|---|---|---|---|---|
| 29 | C₂H₅ | H | H | CH₃ | SCH₃ | O | S | |
| 30 | C₂H₅ | H | H | iC₃H₇ | SCH₃ | O | S | |
| 31 | iC₃H₇ | H | H | CH₃ | SCH₃ | O | S | |
| 32 | iC₃H₇ | H | H | iC₃H₇ | SCH₃ | O | S | |
| 33 | C₂H₅ | H | H | CH₃OCH₂CH₂ | SCH₃ | O | S | |
| 34 | iC₃H₇ | H | H | CH₃OCH₂CH₂ | SCH₃ | O | S | |
| 35 | iC₃H₇ | H | H | -C(CH₃)(CH₃)-CN | SCH₃ | O | S | |
| 36 | iC₃H₇ | H | H | CH₂CCl₃ | SCH₃ | O | S | |
| 37 | sC₄H₉ | H | H | CH₃ | SCH₃ | O | S | |
| 38 | -C(CH₃)(CH₃)-CN | H | H | CH₃ | SCH₃ | O | S | |
| 39 | cyclopropyl | H | H | CH₃ | SCH₃ | O | S | |
| 40 | C₂H₅ | H | H | cyclopropyl | SCH₃ | O | S | |
| 41 | C₂H₅ | H | H | tC₄H₉ | SCH₃ | O | S | |
| 42 | C₂H₅ | C₂H₅ | H | CH₃ | SCH₃ | O | S | |
| 43 | CH₃-CH(CH₃)-CH(CH₃)- | H | H | CH₃ | SCH₃ | O | S | |
| 44 | cyclohexyl-CH₂- | H | H | CH₃ | SCH₃ | O | S | |
| 45 | CH₂-CH=CH₂ | H | H | CH₃ | SCH₃ | O | S | |
| 46 | CH₂-C≡CH | H | H | CH₃ | SCH₃ | O | S | |
| 47 | H | H | H | CH₃ | SCH₃ | O | S | |
| 48 | tC₄H₉ | H | H | CH₃ | SC₂H₅ | O | S | |
| 49 | C₂H₅ | H | H | C₂H₅ | SCH₃ | S | O | |
| 50 | CH₃ | H | H | C₂H₅ | SCH₃ | S | O | |
| 51 | CH₃ | H | H | CH₃ | SCH₃ | S | O | |
| 52 | tC₄H₉ | H | H | CH₃ | SCH₃ | S | O | |
| 53 | C₂H₅ | H | H | CH₃ | SCH₃ | S | O | |
| 54 | C₂H₅ | H | H | iC₃H₇ | SCH₃ | S | O | |
| 55 | iC₃H₇ | H | H | CH₃ | SCH₃ | S | O | |
| 56 | iC₃H₇ | H | H | iC₃H₇ | SCH₃ | S | O | |
| 57 | C₂H₅ | H | H | CH₃OCH₂CH₂ | SCH₃ | S | O | |
| 58 | iC₃H₇ | H | H | CH₃OCH₂CH₂ | SCH₃ | S | O | |
| 59 | iC₃H₇ | H | H | -C(CH₃)(CH₃)-CN | SCH₃ | S | O | |
| 60 | iC₃H₇ | H | H | CH₂CCl₃ | SCH₃ | S | O | |
| 61 | sC₄H₉ | H | H | CH₃ | SCH₃ | S | O | |
| 62 | -C(CH₃)(CH₃)-CN | H | H | CH₃ | SCH₃ | S | O | |
| 63 | cyclopropyl | H | H | CH₃ | SCH₃ | S | O | |
| 64 | C₂H₅ | H | H | cyclopropyl | SCH₃ | S | O | |
| 65 | C₂H₅ | H | H | tC₄H₉ | SCH₃ | S | O | |
| 66 | C₂H₅ | C₂H₅ | H | CH₃ | SCH₃ | S | O | |
| 67 | CH₃-CH(CH₃)-CH(CH₃)- | H | H | CH₃ | SCH₃ | S | O | |
| 68 | cyclohexyl-CH₂- | H | H | CH₃ | SCH₃ | S | O | |
| 69 | CH₂-CH=CH₂ | H | H | CH₃ | SCH₃ | S | O | |
| 70 | CH₂-C≡CH | H | H | CH₃ | SCH₃ | S | O | |
| 71 | H | H | H | CH₃ | SCH₃ | S | O | |
| 72 | tC₄H₉ | H | H | CH₃ | SC₂H₅ | S | O | |
| 73 | C₂H₅ | H | H | C₂H₅ | SCH₃ | S | S | |
| 74 | CH₃ | H | H | C₂H₅ | SCH₃ | S | S | |
| 75 | CH₃ | H | H | CH₃ | SCH₃ | S | S | |
| 76 | tC₄H₉ | H | H | CH₃ | SCH₃ | S | S | |
| 77 | C₂H₅ | H | H | CH₃ | SCH₃ | S | S | |
| 78 | C₂H₅ | H | H | iC₃H₇ | SCH₃ | S | S | |
| 79 | iC₃H₇ | H | H | CH₃ | SCH₃ | S | S | |
| 80 | iC₃H₇ | H | H | iC₃H₇ | SCH₃ | S | S | |
| 81 | C₂H₅ | H | H | CH₃OCH₂CH₂ | SCH₃ | S | S | |
| 82 | iC₃H₇ | H | H | CH₃OCH₂CH₂ | SCH₃ | S | S | |

-continued

| Compound No. | R₁ | R₂ | R₃ | R₄ | R₅ | Y | Z | Physical data |
|---|---|---|---|---|---|---|---|---|
| 83 | iC₃H₇ | H | H | -C(CH₃)₂CN | SCH₃ | S | S | |
| 84 | iC₃H₇ | H | H | CH₂CCl₃ | SCH₃ | S | S | |
| 85 | sC₄H₉ | H | H | CH₃ | SCH₃ | S | S | |
| 86 | -C(CH₃)₂CN | H | H | CH₃ | SCH₃ | S | S | |
| 87 | cyclopropyl | H | H | CH₃ | SCH₃ | S | S | |
| 88 | C₂H₅ | H | H | cyclopropyl | SCH₃ | S | S | |
| 89 | C₂H₅ | H | H | tC₄H₉ | SCH₃ | S | S | |
| 90 | C₂H₅ | C₂H₅ | H | CH₃ | SCH₃ | S | S | |
| 91 | CH₃-CH(CH₃)-CH(CH₃)- | H | H | CH₃ | SCH₃ | S | S | |
| 92 | C₆H₁₁-CH₂- | H | H | CH₃ | SCH₃ | S | S | |
| 93 | CH₂-CH=CH₂ | H | H | CH₃ | SCH₃ | S | S | |
| 94 | CH₂-C≡CH | H | H | CH₃ | SCH₃ | S | S | |
| 95 | H | H | H | CH₃ | SCH₃ | S | S | |
| 96 | tC₄H₉ | H | H | CH₃ | SC₂H₅ | S | S | |
| 97 | C₂H₅ | H | H | CH₃ | OCH₃ | O | O | m.p. 142–144° |
| 98 | C₂H₅ | H | H | C₂H₅ | OCH₃ | O | O | m.p. 110–111° |
| 99 | CH₃ | H | H | CH₃ | OCH₃ | O | O | m.p. 160–163° |
| 100 | C₂H₅ | H | H | iC₃H₇ | OCH₃ | O | O | m.p. 105–107° |
| 101 | iC₃H₇ | H | H | CH₃ | OCH₃ | O | O | m.p. 104–108° |
| 102 | iC₃H₇ | H | H | iC₃H₇ | OCH₃ | O | O | m.p. 119–121° |
| 103 | tC₄H₉ | H | H | CH₃ | OCH₃ | O | O | b.p. 154°/0.001mm |
| 104 | C₂H₅ | H | H | CH₃OCH₂CH₂ | OCH₃ | O | O | m.p. 88–90° |
| 105 | iC₃H₇ | H | H | CH₃OCH₂CH₂ | OCH₃ | O | O | oil |
| 106 | iC₃H₇ | H | H | -C(CH₃)₂CN | OCH₃ | O | O | m.p. 86–90° |
| 107 | iC₃H₇ | H | H | CH₂CCl₃ | OCH₃ | O | O | |
| 108 | sC₄H₉ | H | H | CH₃ | OCH₃ | O | O | |
| 109 | -C(CH₃)₂CN | H | H | CH₃ | OCH₃ | O | O | |
| 110 | cyclopropyl | H | H | CH₃ | OCH₃ | O | O | |
| 111 | C₂H₅ | H | H | cyclopropyl | OCH₃ | O | O | |
| 112 | C₂H₅ | H | H | tC₄H₉ | OCH₃ | O | O | |
| 113 | C₂H₅ | C₂H₅ | H | CH₃ | OCH₃ | O | O | |
| 114 | CH₃-CH(CH₃)-CH(CH₃)- | H | H | CH₃ | OCH₃ | O | O | |
| 115 | C₆H₁₁-CH₂- | H | H | CH₃ | OCH₃ | O | O | |
| 116 | CH₂-CH=CH₂ | H | H | CH₃ | OCH₃ | O | O | |
| 117 | CH₂-C≡CH | H | H | CH₃ | OCH₃ | O | O | |
| 118 | H | H | H | CH₃ | OCH₃ | O | O | |
| 119 | tC₄H₉ | H | H | CH₃ | OC₂H₅ | O | O | |
| 120 | C₂H₅ | H | H | C₂H₅ | OCH₃ | O | S | m.p. 146–148° |
| 121 | C₂H₅ | H | H | CH₃ | OCH₃ | O | S | m.p. 150–159° |
| 122 | CH₃ | H | H | CH₃ | OCH₃ | O | S | |
| 123 | C₂H₅ | H | H | iC₃H₇ | OCH₃ | O | S | |
| 124 | iC₃H₇ | H | H | CH₃ | OCH₃ | O | S | |
| 125 | iC₃H₇ | H | H | iC₃H₇ | OCH₃ | O | S | |
| 126 | tC₄H₉ | H | H | CH₃ | OCH₃ | O | S | |
| 127 | C₂H₅ | H | H | CH₃OCH₂CH₂ | OCH₃ | O | S | |
| 128 | iC₃H₇ | H | H | CH₃OCH₂CH₂ | OCH₃ | O | S | |
| 129 | iC₃H₇ | H | H | -C(CH₃)₂CN | OCH₃ | O | S | |
| 130 | iC₃H₇ | H | H | CH₂CCl₃ | OCH₃ | O | S | |
| 131 | sC₄H₉ | H | H | CH₃ | OCH₃ | O | S | |

-continued

| Compound No. | R₁ | R₂ | R₃ | R₄ | R₅ | Y | Z | Physical data |
|---|---|---|---|---|---|---|---|---|
| 132 | -C(CH₃)₂-CN | H | H | CH₃ | OCH₃ | O | S | |
| 133 | cyclopropyl | H | H | CH₃ | OCH₃ | O | S | m.p. 141–143° |
| 134 | C₂H₅ | H | H | cyclopropyl | OCH₃ | O | S | |
| 135 | C₂H₅ | H | H | tC₄H₉ | OCH₃ | O | S | |
| 136 | C₂H₅ | C₂H₅ | H | CH₃ | OCH₃ | O | S | |
| 137 | CH₃-CH(CH₃)-CH(CH₃)- | H | H | CH₃ | OCH₃ | O | S | |
| 138 | C₆H₁₁-CH₂- | H | H | CH₃ | OCH₃ | O | S | |
| 139 | CH₂-CH=CH₂ | H | H | CH₃ | OCH₃ | O | S | |
| 140 | CH₂-C≡CH | H | H | CH₃ | OCH₃ | O | S | |
| 141 | H | H | H | CH₃ | OCH₃ | O | S | |
| 142 | tC₄H₉ | H | H | CH₃ | OC₂H₅ | O | S | |
| 143 | C₂H₅ | H | H | CH₃ | OCH₃ | S | O | |
| 144 | C₂H₅ | H | H | C₂H₅ | OCH₃ | S | O | |
| 145 | CH₃ | H | H | CH₃ | OCH₃ | S | O | |
| 146 | C₂H₅ | H | H | iC₃H₇ | OCH₃ | S | O | |
| 147 | iC₃H₇ | H | H | CH₃ | OCH₃ | S | O | |
| 148 | iC₃H₇ | H | H | iC₃H₇ | OCH₃ | S | O | |
| 149 | tC₄H₉ | H | H | CH₃ | OCH₃ | S | O | |
| 150 | C₂H₅ | H | H | CH₃OCH₂CH₂ | OCH₃ | S | O | |
| 151 | iC₃H₇ | H | H | CH₃OCH₂CH₂ | OCH₃ | S | O | |
| 152 | iC₃H₇ | H | H | -C(CH₃)₂-CN | OCH₃ | S | O | |
| 153 | iC₃H₇ | H | H | CH₂CCl₃ | OCH₃ | S | O | |
| 154 | sC₄H₉ | H | H | CH₃ | OCH₃ | S | O | |
| 155 | -C(CH₃)₂-CN | H | H | CH₃ | OCH₃ | S | O | |
| 156 | cyclopropyl | H | H | CH₃ | OCH₃ | S | O | |
| 157 | C₂H₅ | H | H | cyclopropyl | OCH₃ | S | O | |
| 158 | C₂H₅ | H | H | tC₄H₉ | OCH₃ | S | O | |
| 159 | C₂H₅ | C₂H₅ | H | CH₃ | OCH₃ | S | O | |
| 160 | CH₃-CH(CH₃)-CH(CH₃)- | H | H | CH₃ | OCH₃ | S | O | |
| 161 | C₆H₁₁-CH₂- | H | H | CH₃ | OCH₃ | S | O | |
| 162 | CH₂-CH=CH₂ | H | H | CH₃ | OCH₃ | S | O | |
| 163 | CH₂-C≡CH | H | H | CH₃ | OCH₃ | S | O | |
| 164 | H | H | H | CH₃ | OCH₃ | S | O | |
| 165 | tC₄H₉ | H | H | CH₃ | OC₂H₅ | S | O | |
| 166 | C₂H₅ | H | H | CH₃ | OCH₃ | S | S | |
| 167 | C₂H₅ | H | H | C₂H₅ | OCH₃ | S | S | |
| 168 | CH₃ | H | H | CH₃ | OCH₃ | S | S | |
| 169 | C₂H₅ | H | H | iC₃H₇ | OCH₃ | S | S | |
| 170 | iC₃H₇ | H | H | CH₃ | OCH₃ | S | S | |
| 171 | iC₃H₇ | H | H | iC₃H₇ | OCH₃ | S | S | |
| 172 | tC₄H₉ | H | H | CH₃ | OCH₃ | S | S | |
| 173 | C₂H₅ | H | H | CH₃OCH₂CH₂ | OCH₃ | S | S | |
| 174 | iC₃H₇ | H | H | CH₃OCH₂CH₂ | OCH₃ | S | S | |
| 175 | iC₃H₇ | H | H | -C(CH₃)₂-CN | OCH₃ | S | S | |
| 176 | iC₃H₇ | H | H | CH₂CCl₃ | OCH₃ | S | S | |
| 177 | sC₄H₉ | H | H | CH₃ | OCH₃ | S | S | |
| 178 | -C(CH₃)₂-CN | H | H | CH₃ | OCH₃ | S | S | |
| 179 | cyclopropyl | H | H | CH₃ | OCH₃ | S | S | |

-continued

| Compound No. | R₁ | R₂ | R₃ | R₄ | R₅ | Y | Z | Physical data |
|---|---|---|---|---|---|---|---|---|
| 180 | C₂H₅ | H | H |  | OCH₃ | S | S | |
| 181 | C₂H₅ | H | H | tC₄H₉ | OCH₃ | S | S | |
| 182 | C₂H₅ | C₂H₅ | H | CH₃ | OCH₃ | S | S | |
| 183 | CH₃—CH—CH<br>        \|    \|<br>        CH₃ CH₃ | H | H | CH₃ | OCH₃ | S | S | |
| 184 | 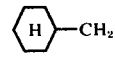 | H | H | CH₃ | OCH₃ | S | S | |
| 185 | CH₂—CH=CH₂ | H | H | CH₃ | OCH₃ | S | S | |
| 186 | CH₂—C≡CH | H | H | CH₃ | OCH₃ | S | S | |
| 187 | H | H | H | CH₃ | OCH₃ | S | S | |
| 188 | tC₄H₉ | H | H | CH₃ | OC₂H₅ | S | S | |
| 189 | C₂H₅ | H | H | CH₃ | N₃ | O | O | m.p. 153–154° |
| 190 | CH₃ | H | H | C₂H₅ | N₃ | O | O | |
| 191 | CH₃ | H | H | CH₃ | N₃ | O | O | |
| 192 | C₂H₅ | H | H | iC₃H₇ | N₃ | O | O | |
| 193 | iC₃H₇ | H | H | CH₃ | N₃ | O | O | m.p. 179–182° |
| 194 | iC₃H₇ | H | H | iC₃H₇ | N₃ | O | O | m.p. 137–138° |
| 195 | tC₄H₉ | H | H | CH₃ | N₃ | O | O | m.p. 96–98° |
| 196 | C₂H₅ | H | H | CH₃OCH₂CH₂ | N₃ | O | O | m.p. 104–106° |
| 197 | iC₃H₇ | H | H | CH₃OCH₂CH₂ | N₃ | O | O | m.p. 89–90° |
| 198 | iC₃H₇ | H | H |  | N₃ | O | O | m.p. 95–57° |
| 199 | iC₃H₇ | H | H | CH₂CCl₃ | N₃ | O | O | m.p. 106–108 |
| 200 | sC₄H₉ | H | H | CH₃ | N₃ | O | O | m.p. 154–156° |
| 201 | 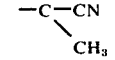 | H | H | CH₃ | N₃ | O | O | |
| 202 |  | H | H | CH₃ | N₃ | O | O | m.p. 176–178° |
| 203 | C₂H₅ | H | H |  | N₃ | O | O | |
| 204 | C₂H₅ | H | H | tC₄H₉ | N₃ | O | O | |
| 205 | C₂H₅ | C₂H₅ | H | CH₃ | N₃ | O | O | |
| 206 | CH₃—CH—CH<br>        \|    \|<br>        CH₃ CH₃ | H | H | CH₃ | N₃ | O | O | |
| 207 |  | H | H | CH₃ | N₃ | O | O | |
| 208 | CH₂—CH=CH₂ | H | H | CH₃ | N₃ | O | O | |
| 209 | CH₂—C≡CH | H | H | CH₃ | N₃ | O | O | |
| 210 | H | H | H | CH₃ | N₃ | O | O | |
| 211 | C₂H₅ | H | H | C₂H₅ | N₃ | O | S | m.p. 177–178° |
| 212 | CH₃ | H | H | C₂H₅ | N₃ | O | S | m.p. 215 (decomp.) |
| 213 | C₂H₅ | H | H | CH₃ | N₃ | O | S | |
| 214 | CH₃ | H | H | CH₃ | N₃ | O | S | |
| 215 | C₂H₅ | H | H | iC₃H₇ | N₃ | O | S | |
| 216 | iC₃H₇ | H | H | CH₃ | N₃ | O | S | |
| 217 | iC₃H₇ | H | H | iC₃H₇ | N₃ | O | S | |
| 218 | tC₄H₉ | H | H | CH₃ | N₃ | O | S | |
| 219 | C₂H₅ | H | H | CH₃OCH₂CH₂ | N₃ | O | S | m.p. 189–190° |
| 220 | iC₃H₇ | H | H | CH₃OCH₂CH₂ | N₃ | 0 | S | |
| 221 | iC₃H₇ | H | H | 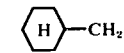 | N₃ | O | S | |
| 222 | iC₃H₇ | H | H | CH₂CCl₃ | N₃ | O | S | |
| 223 | sC₄H₉ | H | H | CH₃ | N₃ | O | S | |
| 224 |  | H | H | CH₃ | N₃ | O | S | |
| 225 | 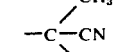 | H | H | CH₃ | N₃ | O | S | |
| 226 | C₂H₅ | H | H | 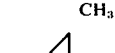 | N₃ | O | S | |
| 227 | C₂H₅ | H | H | tC₄H₉ | N₃ | O | S | |
| 228 | C₂H₅ | C₂H₅ | H | CH₃ | N₃ | O | S | |
| 229 | CH₃—CH—CH<br>        \|    \|<br>        CH₃ CH₃ | H | H | CH₃ | N₃ | O | S | |

-continued

| Compound No. | $R_1$ | $R_2$ | $R_3$ | $R_4$ | $R_5$ | Y | Z | Physical data |
|---|---|---|---|---|---|---|---|---|
| 230 | benzyl (C$_6$H$_5$-CH$_2$-) | H | H | CH$_3$ | N$_3$ | O | S | |
| 231 | CH$_2$-CH=CH$_2$ | H | H | CH$_3$ | N$_3$ | O | S | |
| 232 | CH$_2$-C≡CH | H | H | CH$_3$ | N$_3$ | O | S | |
| 233 | H | H | H | CH$_3$ | N$_3$ | S | O | |
| 234 | C$_2$H$_5$ | H | H | C$_2$H$_5$ | N$_3$ | S | O | |
| 235 | C$_2$H$_5$ | H | H | CH$_3$ | N$_3$ | S | O | |
| 236 | CH$_3$ | H | H | C$_2$H$_5$ | N$_3$ | S | O | |
| 237 | CH$_3$ | H | H | CH$_3$ | N$_3$ | S | O | |
| 238 | C$_2$H$_5$ | H | H | iC$_3$H$_7$ | N$_3$ | S | O | |
| 239 | iC$_3$H$_7$ | H | H | CH$_3$ | N$_3$ | S | O | |
| 240 | iC$_3$H$_7$ | H | H | iC$_3$H$_7$ | N$_3$ | S | O | |
| 241 | tC$_4$H$_9$ | H | H | CH$_3$ | N$_3$ | S | O | |
| 242 | C$_2$H$_5$ | H | H | CH$_3$OCH$_2$CH$_2$ | N$_3$ | S | O | |
| 243 | iC$_3$H$_7$ | H | H | CH$_3$OCH$_2$CH$_2$ | N$_3$ | S | O | |
| 244 | iC$_3$H$_7$ | H | H | -C(CH$_3$)$_2$CN | N$_3$ | S | O | |
| 245 | iC$_3$H$_7$ | H | H | CH$_2$CCl$_3$ | N$_3$ | S | O | |
| 246 | sC$_4$H$_9$ | H | H | CH$_3$ | N$_3$ | S | O | |
| 247 | -C(CH$_3$)$_2$CN | H | H | CH$_3$ | N$_3$ | S | O | |
| 248 | cyclopropyl | H | H | CH$_3$ | N$_3$ | S | O | |
| 249 | C$_2$H$_5$ | H | H | cyclopropyl | N$_3$ | S | O | |
| 250 | C$_2$H$_5$ | H | H | tC$_4$H$_9$ | N$_3$ | S | O | |
| 251 | C$_2$H$_5$ | C$_2$H$_5$ | H | CH$_3$ | N$_3$ | S | O | |
| 252 | CH$_3$-CH(CH$_3$)-CH(CH$_3$)- | H | H | CH$_3$ | N$_3$ | S | O | |
| 253 | benzyl (C$_6$H$_5$-CH$_2$-) | H | H | CH$_3$ | N$_3$ | S | O | |
| 254 | CH$_2$-CH=CH$_2$ | H | H | CH$_3$ | N$_3$ | S | O | |
| 255 | CH$_2$-C≡CH | H | H | CH$_3$ | N$_3$ | S | O | |
| 256 | H | H | H | CH$_3$ | N$_3$ | S | S | |
| 257 | C$_2$H$_5$ | H | H | C$_2$H$_5$ | N$_3$ | S | S | |
| 258 | C$_2$H$_5$ | H | H | CH$_3$ | N$_3$ | S | S | |
| 259 | CH$_3$ | H | H | C$_2$H$_5$ | N$_3$ | S | S | |
| 260 | CH$_3$ | H | H | CH$_3$ | N$_3$ | S | S | |
| 261 | C$_2$H$_5$ | H | H | iC$_3$H$_7$ | N$_3$ | S | S | |
| 262 | iC$_3$H$_7$ | H | H | CH$_3$ | N$_3$ | S | S | |
| 263 | iC$_3$H$_7$ | H | H | iC$_3$H$_7$ | N$_3$ | S | S | |
| 264 | tC$_4$H$_9$ | H | H | CH$_3$ | N$_3$ | S | S | |
| 265 | C$_2$H$_5$ | H | H | CH$_3$OCH$_2$CH$_2$ | N$_3$ | S | S | |
| 266 | iC$_3$H$_7$ | H | H | CH$_3$OCH$_2$CH$_2$ | N$_3$ | S | S | |
| 267 | iC$_3$H$_7$ | H | H | -C(CH$_3$)$_2$CN | N$_3$ | S | S | |
| 268 | iC$_3$H$_7$ | H | H | CH$_2$CCl$_3$ | N$_3$ | S | S | |
| 269 | sC$_4$H$_9$ | H | H | CH$_3$ | N$_3$ | S | S | |
| 270 | -C(CH$_3$)$_2$CN | H | H | CH$_3$ | N$_3$ | S | S | |
| 271 | cyclopropyl | H | H | CH$_3$ | N$_3$ | S | S | |
| 272 | C$_2$H$_5$ | H | H | cyclopropyl | N$_3$ | S | S | |
| 273 | C$_2$H$_5$ | H | H | tC$_4$H$_9$ | N$_3$ | S | S | |
| 274 | C$_2$H$_5$ | C$_2$H$_5$ | H | CH$_3$ | N$_3$ | S | S | |
| 275 | CH$_3$-CH(CH$_3$)-CH(CH$_3$)- | H | H | CH$_3$ | N$_3$ | S | S | |
| 276 | benzyl (C$_6$H$_5$-CH$_2$-) | H | H | CH$_3$ | N$_3$ | S | S | |
| 277 | CH$_2$-CH=CH$_2$ | H | H | CH$_3$ | N$_3$ | S | S | |
| 278 | CH$_2$-C≡CH | H | H | CH$_3$ | N$_3$ | S | S | |
| 279 | H | H | H | CH$_3$ | SCH$_3$ | O | O | |
| 280 | tC$_4$H$_9$ | H | CH$_3$ | CH$_3$ | SCH$_3$ | O | O | |
| 281 | tC$_4$H$_9$ | H | C$_2$H$_5$ | CH$_3$ | SCH$_3$ | O | O | |

-continued

| Compound No. | R₁ | R₂ | R₃ | R₄ | R₅ | Y | Z | Physical data |
|---|---|---|---|---|---|---|---|---|
| 282 | $tC_4H_9$ | H | $CH_3$ | $CH_3$ | $SCH_3$ | O | S | |
| 283 | $tC_4H_9$ | H | $C_2H_5$ | $CH_3$ | $SCH_3$ | O | S | |
| 284 | $tC_4H_9$ | H | $CH_3$ | $CH_3$ | $OCH_3$ | O | O | |
| 285 | $tC_4H_9$ | H | $C_2H_5$ | $CH_3$ | $OCH_3$ | O | O | |
| 286 | $tC_4H_9$ | H | $CH_3$ | $CH_3$ | $N_3$ | O | O | |
| 287 | $iC_3H_7$ | H | $C_3H_5$ | $CH_3$ | $SCH_3$ | O | O | |
| 288 | $iC_3H_7$ | H | $C_3H_5$ | $CH_3$ | $OCH_3$ | O | O | |
| 289 | $iC_3H_7$ | H | $C_3H_5$ | $CH_3$ | $N_3$ | O | O | |
| 290 | $iC_3H_7$ | H | $CH_3$ | $CH_3$ | $SCH_3$ | O | O | |
| 291 | $iC_3H_7$ | H | $CH_3$ | $CH_3$ | $OCH_3$ | O | O | |
| 292 | $iC_3H_7$ | H | $CH_3$ | $CH_3$ | $N_3$ | O | O | |
| 293 | $iC_3H_7$ | H | $n\text{-}C_3H_7$ | $CH_3$ | $OCH_3$ | O | O | |
| 294 | $iC_3H_7$ | H | $n\text{-}C_3H_7$ | $CH_3$ | $SCH_3$ | O | O | |
| 295 | $iC_3H_7$ | H | $nC_3H_7$ | $CH_3$ | $N_3$ | O | O | |
| 296 |  | H | $C_3H_5$ | $CH_3$ | $SCH_3$ | O | O | |
| 297 |  | H | $C_3H_5$ | $CH_3$ | $OCH_3$ | O | O | |
| 298 |  | H | $C_3H_5$ | $CH_3$ | $N_3$ | O | O | |
| 299 | $C_3H_5$ | H | $C_3H_5$ | $CH_3$ | $OCH_3$ | O | O | |
| 300 | $C_3H_5$ | H | $C_3H_5$ | $CH_3$ | $SCH_3$ | O | O | |
| 301 | $C_3H_5$ | H | $C_3H_5$ | $CH_3$ | $N_3$ | O | O | |
| 302 | $CH_3-O(CH_2)_3$ | H | $C_3H_5$ | $CH_3$ | $SCH_3$ | O | O | |
| 303 | $CH_3-O-(CH_2)_3$ | H | $C_3H_5$ | $CH_3$ | $OCH_3$ | O | O | |
| 304 | $CH_3-O-(CH_2)_3$ | H | $C_3H_5$ | $CH_3$ | $N_3$ | O | O | |
| 305 | $NC-\underset{CH_3}{\overset{CH_3}{C}}-$ | H | $C_3H_5$ | $CH_3$ | $SCH_3$ | O | O | |
| 306 | $NC-\underset{CH_3}{\overset{CH_3}{C}}-$ | H | $C_3H_5$ | $CH_3$ | $OCH_3$ | O | O | |
| 307 | $NC-\underset{CH_3}{\overset{CH_3}{C}}-$ | H | $C_3H_5$ | $CH_3$ | $N_3$ | O | O | |
| 308 | $CH_3-O(CH_2)_3N$ | H | $C_3H_5$ | $CH_3$ | $SCH_3$ | O | O | |
| 309 | $CH_3-O(CH_2)_3N$ | H | $C_3H_5$ | $CH_3$ | $OCH_3$ | O | O | |
| 310 | $CH_3-O(CH_2)_3N$ | H | $C_3H_5$ | $CH_3$ | $N_3$ | O | O | |
| 311 | sec. $C_4H_5$ | H | $C_3H_5$ | $CH_3$ | $SCH_3$ | O | O | |
| 312 | sec. $C_4H_5$ | H | $C_3H_5$ | $CH_3$ | $OCH_3$ | O | O | |
| 313 | sec. $C_4H_5$ | H | $C_3H_5$ | $CH_3$ | $N_3$ | O | O | |
| 314 | $i\text{-}C_3H_7$ | H | $i\text{-}C_3H_7$ | $CH_3$ | $SC_2H_5$ | O | O | |
| 315 | $C_2H_5$ | H | $(t)C_4H_9$ | $CH_3$ | $OCH_3$ | O | O | m.p. 74–76° |
| 316 | $C_2H_5$ | H | $(t)C_4H_9$ | $CH_3$ | $SCH_3$ | O | O | m.p. 89–90° |
| 317 | $CH_3$ | H | $(t)C_4H_9$ | $CH_3$ | $SCH_3$ | O | O | |
| 318 | $C_2H_5$ | H | $(t)C_4H_9$ | $CH_3$ | $SCH_3$ | O | O | |
| 319 | $CH_3$ | H | $(t)C_4H_9$ | $CH_3$ | $SCH_3$ | O | S | |
| 320 | $C_2H_5$ | H | $(t)C_4H_9$ | $CH_3$ | $SCH_3$ | O | S | |
| 321 | $CH_3$ | H | $(t)C_4H_9$ | $CH_3$ | $OCH_3$ | O | O | |
| 322 | $C_2H_5$ | H | $(t)C_4H_9$ | $CH_3$ | $OCH_3$ | O | O | |
| 323 | $CH_3$ | H | $(t)C_4H_9$ | $CH_3$ | $N_3$ | O | O | |
| 324 | $C_2H_5$ | H |  | $CH_3$ | $OCH_3$ | O | O | |
| 325 | $C_2H_5$ | H |  | $CH_3$ | $SCH_3$ | O | O | |
| 326 | $C_2H_5$ | H |  | $CH_3$ | $N_3$ | O | O | |
| 327 | $C_2H_4$ | $C_2H_5$ | $C_2H_5$ | $CH_3$ | $SCH_3$ | O | O | |
| 328 | $C_2H_5$ | $C_2H_5$ | $C_2H_5$ | $CH_3$ | $OCH_3$ | O | O | |
| 329 | $C_2H_5$ | H | $iC_3H_7$ | $CH_3$ | $SCH_3$ | O | O | |
| 330 | $C_2H_5$ | H | $iC_3H_7$ | $CH_3$ | $OCH_3$ | O | O | |
| 331 | $C_2H_5$ | H | $(t)C_4H_9$ | $CH_3$ | $SCH_3$ | O | O | |
| 332 | $C_2H_5$ | H | $(t)C_4H_9$ | $CH_3$ | $OCH_3$ | O | O | |
| 333 | $C_2H_5$ | H | $NC-\underset{CH_3}{\overset{CH_3}{C}}-$ | $CH_3$ | $SCH_3$ | O | O | |

EXAMPLE 3

Fungicidal action

Action against Erysiphe cichoracearum on Cucurbita pepo

A spray suspension produced from a wettable powder of the active substance (0.01% of active substance relative to the volume of soil) is applied to zucchetti plants in the cotyledon-stage; care is taken to ensure that the spray suspension does not come into contact with the parts of the plants above the soil. After 48 hours, the treated plants are infested by being dusted with conidiospores of the fungus. The infested plants are kept in a greenhouse at about 22° C, and the fungus infestation is assessed after 10 days.

With the use of Compound No. 98, the infestation of the plants is less than 20%.

A similar action was exhibited by further compounds embraced by the formula I.

EXAMPLE 4

Insecticidal action

Action against Musca domestica

An amount in each case of 50 g of CSMA maggot substrate is weighed off in beakers. For each active substance, 2.5 ml of a 1% acetonic solution of the respective substance is transferred by pipet twice to 50 g of maggot substrate each time. After a thorough mixing of the treated substrate, the solvent is allowed to evaporate off. There are then deposited per active substance in each case 25 one-, two- and three-day-old maggots and about 50 fly eggs. After completion of pupation, the pupae are flushed out and counted. After a period of ten days, the number of emerged flies is counted and hence any effect on metamorphosis is established.

With use of the Compound No. 189, the number of emerged flies is reduced to approximately 0 (4 repeats).

A similar action is exhibited by further compounds embraced by the Formula I.

EXAMPLE 5

Action in breadth against monocotyledonous and dicotyledonous weeds in selected useful crops (pre-emergence treatment).

Immediately after the sowing of the test plants in seed trays, the active substances are applied as an aqueous suspension, obtained from a 25% wettable powder, to the surface of the soil in the trays, so that an applied amount equivalent to 2 kg per hectare is ensured. The seed trays are then kept at 22 to 23° C with 50 to 70% relative humidity. The test results are evaluated after 28 days.

USEFUL PLANTS maize, rice, cotton.

WEEDS

Avena fatua, Lolium perenne, Alopecurus myosuroides, Setaria italica, Echinochlora crus galli, Amarantus retroflexus, Sinapis alba, Ipomoea purpurea.

With use of the Compound No. 1, weeds are damaged to the extent of 50% or more (i.e. irreversible damage), while useful plants are only slightly affected (reversible damage).

A similar action is exhibited by further compounds embraced by the formula I.

EXAMPLE 6

Herbicidal action with application of the active substances after emergence (post-emergence) of the plants.

The test plants are treated in the 2-4-leaf stage with aqueous suspensions of the active substances, obtained from 25% emulsion concentrates. The applied amount corresponds to 4 kg of active substance per hectare.

The following are used as test plants:

| | |
|---|---|
| Setaria italica | Stellaria media |
| Lolium perenne | Gossypium hirsutum (cotton) |
| Sinapis alba | Phaseolus vulgares |

After the treatment, the plants are kept for 14 days in a greenhouse under normal conditions.

With use of the Compound No. 3, weeds are damaged to the extent of at least 50% or more (irreversible damage), while cotton is affected only slightly (reversible damage).

Other compounds embraced by the formula I have a similar action.

EXAMPLE 7

Growth inhibition in the case of grasses (post-emergence treatment).

Seeds of the grasses Lolium perenne, Poa pratensis, Festuca ovina and Dactylis glomerata are sown in plastics trays containing a soil/peat/sand mixture. After three weeks, the emerged grasses are cut back to 4 cm above the soil, and two days later sprayed with an aqueous spray liquor of the active substance. The amount of active substance is equivalent to 5 kg of active substance per hectare. The growth of the grasses is evaluated 14 days after application according to the following linear scale of values.

1 = severe inhibition (no growth from time of application),

9 = no inhibition (growth as in the case of the control specimens).

With use of the Compound No. 189 as active substance, a severe inhibition of growth is observed (values between 1 and 4).

A similar action is exhibited by further compounds embraced by the formula I.

I claim:

1. A compound of the formula I

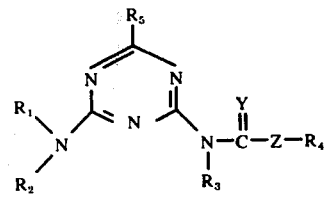

wherein $R_1$ represents hydrogen, $C_1$–$C_6$-alkyl, $C_3$–$C_6$-cycloalkyl, $C_4$–$C_7$-cycloalkylalkyl, $C_2$–$C_6$-alkoxyalkyl, $C_2$–$C_6$-cyanoalkyl, $C_3$–$C_4$-alkenyl or $C_3$–$C_4$-alkynyl, $R_2$ represents hydrogen or $C_1$–$C_6$-alkyl, $R_3$ represents hydrogen or $C_1$–$C_6$-alkyl, $R_4$ represents $C_1$–$C_6$-alkyl, $C_3$–$C_6$-cycloalkyl, $C_2$–$C_6$-alkoxyalkyl, $C_2$–$C_6$-cyanoalkyl or $C_1$–$C_6$-halogenoalkyl, $R_5$ represents methoxy, ethoxy, methylthio, ethylthio or azido ($N_3$), and Y and Z each independently represent sulphur or oxygen.

2. As a compound according to claim 1 2-methylthio-4-ethylamino-6-methoxy-carbamido-s-triazine.

3. As a compound according to claim 1 2-methylthio-4-isopropylamino-6-methoxy-carbamido-s-triazine.

4. As a compound according to claim 1 2-methoxy-4-isopropylamino-6-methoxy-carbamido-s-triazine.

5. As a compound according to claim 1 2-azido-4-t.butylamino-6-methoxy-carbamido-s-triazine.

6. As a compound according to claim 1 2-methylthio-4-ethylamino-6-N-t.butyl-methoxy-carbamido-s-triazine.

7. As a compound according to claim 1 2-methylthio-4-t.butylamino-6-N-methoxy-carbamido-s-triazine.

8. A herbicidal composition, particularly for the control of gramineous and broad-leaved weeds in cultivated crops, which composition comprises as active substance a herbicidally effective amount of a compound of claim 1, together with a suitable inert carrier therefor.

9. A method for selectively controlling weeds in cultivated crops comprising applying to a crop area a herbicidally effective amount of a compound of claim 1.

* * * * *